United States Patent [19]

Markosian et al.

[11] Patent Number: 5,071,247
[45] Date of Patent: Dec. 10, 1991

[54] METHOD FOR ANALYSIS OF BLOOD PLATELET AGGREGATIONS AND APPARATUS THEREFOR

[76] Inventors: Ruben A Markosian, Leningradskoe shosse,8/2,kv. 345; Zufar A. Gabbasov, ulitsa Malava Bronnava,13,kv. 17; Evgeny G. Popov, ulitsa Osennaya,2,kv. 31; Ilya J. Gavrilov, ulitsa Osennaya,2,kv. 51; Evgeny Y. Pozin, Rublevskoe shosse,38,korpus 2,kv. 544; Sergei D. Proshkin, ulitsa Osennaya,2,kv, 131, all of, Moscow, U.S.S.R.

[21] Appl. No.: 449,863
[22] PCT Filed: Apr. 20, 1988
[86] PCT No.: PCT/SU88/00090
§ 371 Date: Dec. 18, 1989
§ 102(e) Date: Dec. 18, 1989
[87] PCT Pub. No.: WO89/10562
PCT Pub. Date: Nov. 2, 1989
[51] Int. Cl.$^5$ .................... G01N 33/48; G01N 21/90; H01J 40/14
[52] U.S. Cl. ...................... 356/39; 356/40; 356/427; 250/214 L
[58] Field of Search ............ 356/427, 415, 39, 40, 356/335, 336; 250/214 D, 214 C, 214 L

[56] References Cited

U.S. PATENT DOCUMENTS

| | | | |
|---|---|---|---|
| 3,768,706 | 8/1971 | Hanson | 250/214 L |
| 3,989,382 | 1/1976 | Kent et al. | 356/39 |
| 4,066,360 | 1/1978 | Breddin et al. | 356/39 |
| 4,116,564 | 9/1978 | Renaud et al. | 356/39 |
| 4,135,818 | 1/1979 | Kent et al. | 356/39 |
| 4,352,557 | 10/1982 | Schmid-Schönbein | 356/39 |
| 4,577,964 | 3/1925 | Hansen, Jr. | 356/39 |
| 4,641,658 | 2/1987 | Lepper | 356/39 |
| 4,657,383 | 4/1987 | Bellhouse | 356/39 |

FOREIGN PATENT DOCUMENTS

| | | |
|---|---|---|
| 1024841 | 6/1983 | U.S.S.R. |
| 1112278 | 9/1984 | U.S.S.R. |
| 1345115 | 10/1987 | U.S.S.R. |

OTHER PUBLICATIONS

The Heathway Machinery Co. Ltd.-Aggregation of Blood Platelets by Adenosine.
Diphosphaite and Ies Reversal-vol. 194, No. 4832-Jun. 9, 1962.

Primary Examiner—Vincent P. McGraw
Assistant Examiner—LaCharles Keesce
Attorney, Agent, or Firm—Burgess, Ryan & Wayne

[57] ABSTRACT

A method for the analysis of blood platelet aggregations consists in that concurrently two parameters are measured the mean intensity and the RMS deviation of intensity of the light flux which had been passed through a blood sample (12) from said means intensity, which is caused by fluctuations of the amount of blood platelets or their aggregations in the optical channel (10), which are used to find the mean radius and concentration of blood platelets in the blood sample (12) being tested. The apparatus also comprises a source (6) of the light flux, a photoreceiver (11), units (17 and 19) to form the mean intensity and the RMS deviation of current intensity from the means intensity, and a unit (20) for determination of parameters of a blood platelet aggregation.

13 Claims, 4 Drawing Sheets

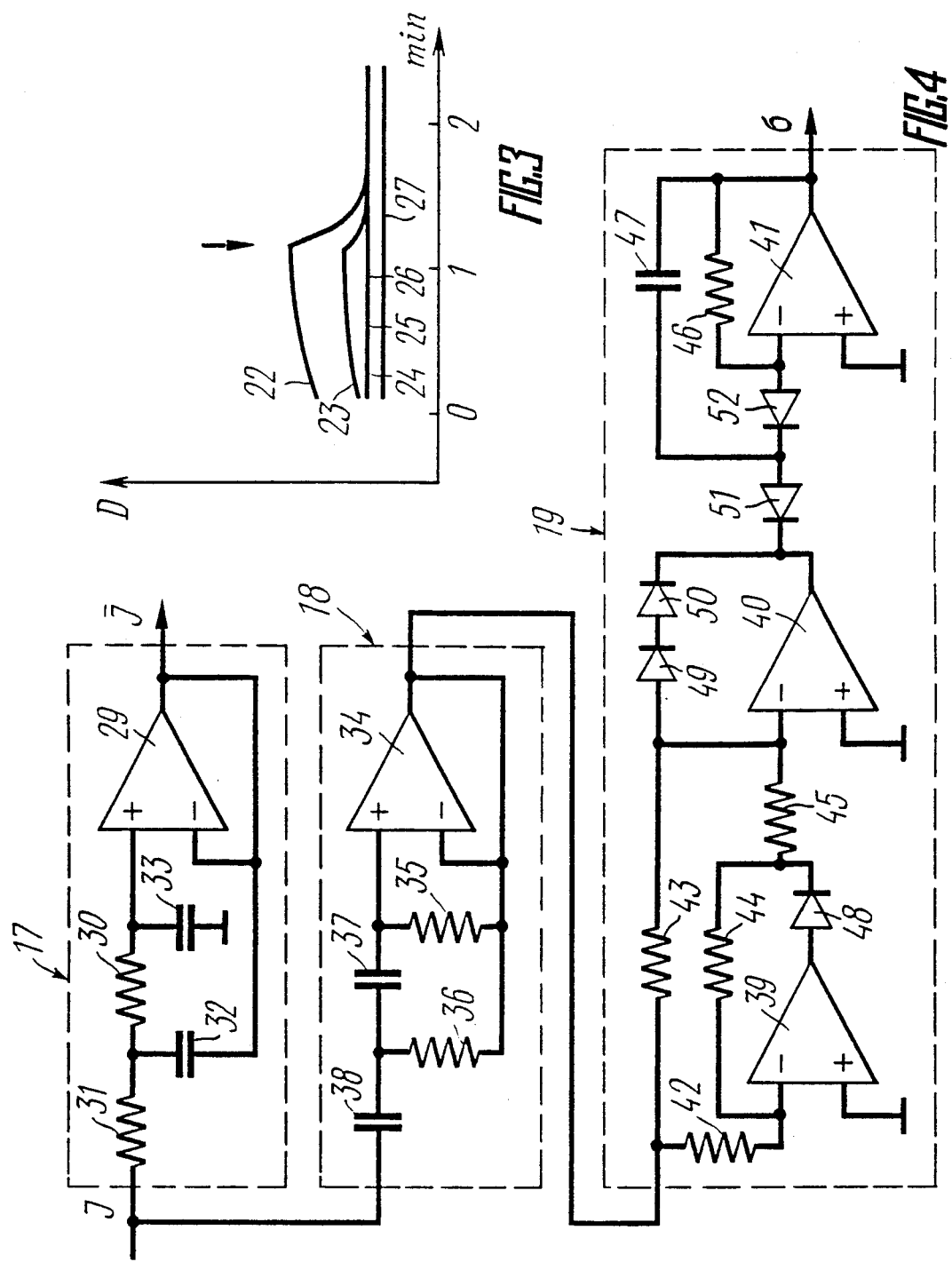

METHOD FOR ANALYSIS OF BLOOD PLATELET AGGREGATIONS AND APPARATUS THEREFOR

BACKGROUND OF THE INVENTION

1. Field of the Invention

This invention relates to medical instrumentation and, in particular, to methods for the analysis of aggregations of thrombocytes also known as blood platelets and devices utilizing this method.

2. Description of the Related Art

Blood cells are known to form aggregates in response to some physiological agents, referred to as aggregation inducers hereinbelow, such as: ADP, platelet activating factor, thrombin, collagen, thromboxane $A_2$, and others. The ability to form aggregates makes platelets the leading factor in triggering the hemostasis mechanisms. Any disruption in the functional activity of blood platelets lead to pathological changes. Analysis of spontaneous or induced aggregation of blood platelets in response to the inducer action makes it possible to diagnose various pathological conditions associated with disruptions of the cell link of hemostasis. It is important that spontaneous aggregation of thrombocytes or large-size aggregations caused by standard action of an aggregation inducer creates the tendency for thromboses, while a decrease in or the absence of a response to such action creates a tendency to bleeding. Concentration of blood cells, particularly platelets, is also an indication of the physiological condition. Thus, a decrease in concentration of circulating platelets may occur during severe toxicosses, disseminated intravascular coagulation of blood, serious and vast injuries, irregular thrombocytopoiesis, and some other deseases. A change in the concentration of platelets during their in vivo aggregation is a diagnostic indication of the condition of the hemostasis system of a body.

Known in the art are several methods for the analysis of thrombocyte aggregation such as optical microscopy, electronic microscopy and conductometric platelet count. These methods are based on direct counting of the number of thrombocytes and determination of distribution of aggregates in accordance with size in appropriately prepared blood samples. However, methods of preparation of blood samples cause substantial errors in the results because of the action of substances, and in particular fixatives, dyes and the like upon blood cells. In addition, these methods are very labour-consuming and unsuitable for such a rapidly occurring process as aggregation of thrombocytes.

The most similar to the method according to the invention is a photometric method for the analysis of thrombocyte aggregation, comprising measuring intensity of light flux passed through a thrombocyte suspension sample. A standard platelet rich plasma is turbid because of the presence of thrombocytes in the suspension. The value of intensity of light passed through the sample is used for determining concentration of thrombocytes. When aggregates are formed, turbidity decreases, and this is used for recording aggregation. For carrying out the method, a blood sample is illuminated with a light beam, and intensity of light flux passed through the sample is recorded. A change in the light flux passed through the sample during aggregation of thrombocytes gives a typical "picture" of aggregation, and the kinetics and degree of aggregation of thrombocytes are evaluated by maximum increase in light transmission (Journal of Physiology, vol. 162, 1962, London, Born B.V.R. Quantitative Investigation into the Aggregation of Blood Platelets, p. 67).

Known in the art are apparatuses used for carrying out the above described method. They comprise a light flux source, a means for holding a blood sample and for stirring it, and a photosensitive member converting light flux passed through the blood sample into an electric signal.

Thus known in the art is an apparatus for the investigation into aggregation with an automatic ranging of an output signal in which a reference signal is in the form of an electric signal corresponding to a light transmission of an autologous sample of platelet poor plasma. The apparatus has two cell compartments, a sample of platelet rich plasma being placed in one compartment and a sample of platelet poor plasma being placed in the other compartment (U.S. Pat. Nos. 4,135,818; 3,989,382).

Also known in the art is an apparatus for measuring thrombocyte aggregation in which a means for containing a sample of thrombocytes comprises a hollow cylinder, and the sample is moved by rotating the cylinder about its axis (U.S. Pat. No. 4,066,360).

In addition, known in the art is an apparatus for investigating into blood properties making use of a light source in the form of a lamp, a cell compartment and a magnetic stirrer positioned on the bottom wall of the cell compartment. Light flux passed through the sample is converted into an electric signal in a photo receiver. This signal corresponds to intensity of the light flux. This apparatus can be used for the analysis of thrombocyte aggregation only without any modifications (U.S. Pat. No. 4,116,564).

One of disadvantages of the prior art method and of apparatuses for carrying out this method resides in the fact that it is not possible to determine size of forming aggregates by a change in light transmission of a sample of blood plasma rich in thrombocytes. This is due to the fact that optical density of a sample is not unambiguously related to the size of forming aggregates. It may occur that two samples will differ in the number of thrombocytes forming aggregates and in the size of the formed aggregates, yet the sample being of one and the same optical density. The shape of thrombocytes also substantially effect optical density. A change of thrombocytes from flat discs to round shape change optical density of a sample by 30–40%. This hampers differential diagnostics of increased activity of thrombocytes in each specific case. In addition, the dependence of reading of the prior art method on light absorption by the medium (blood plasma) makes technical implementation of the method very complicated.

The abovedescribed method and apparatuses have a certain threshold of sensitivity. This does not allow spontaneous aggregation of thrombocytes and aggregation after the action of activators in low concentrations when an average number of thrombocytes in an aggregate does not exceed 100-200. Low sensitivity hampers or even makes it impossible in a number of cases to diagnose hyperactivity of thrombocytes. Moveover, it is inducers in low concentrations that can appear in the actual vessel blood flow, and the inhibiting effect of certain medicines on the aggregation can be detected after the action of such physiological concentrations of inducers.

The optical density of a sample depends not only on particle concentration, but also on optical properties of particles proper and their environment as well as on the structure of an optical channel of the apparatus. Consequently, it is not possible to determine with adequate accuracy concentration of cells by light transmission of the sample.

SUMMARY

It is an object of the invention to provide a method and apparatus for the analysis of thrombocyte aggregation which make it possible to determine size of forming aggregates and to determine with high accuracy concentration of thrombocytes irrespective of light absorption by the medium and shape condition of thrombocytes owing to the measurement of different parameters of light flux passed through the sample.

These and other objects are accomplished by a method for the analysis of thrombocyte aggregation, comprising causing light flux to pass through a blood sample containing thrombocytes and/or their aggregates and measuring parameters of the light flux passed through the blood sample. According to the invention, the method comprises forming an optical channel with desired parameters out of the light flux which is caused to pass through the blood sample, cause thrombocytes and/or their aggregates to move in the blood sample through the optical channel, measuring the mean intensity of the light flux passed through the blood sample and concurrently measuring the rms deviation of intensity of the light flux from the mean intensity caused by fluctuations of the number of thrombocytes and/or their aggregates in the optical channel and determining the mean radius of thrombocytes and or their aggregates and/or concentration of thrombocytes in the blood sample on the basis of the mean value of intensity and rms deviation of intensity of the transmitted light flux.

For determining the mean radius of thrombocytes and/or their aggregates, the use may be made of the value of relative dispersion of fluctuations of the light flux passed through the blood sample which is determined as the square of the ratio of the rms deviation of intensity to the mean value of intensity.

It is preferred that, for determining concentration of thrombocytes, the use be made of the ratio of the square of the difference between logarithms of the mean intensity of the light flux passed through the blood sample and intensity of the light flux in the absence of thrombocytes in the blood sample to the relative dispersion of fluctuations of the light flux.

It is preferred, for a more accurate determination of the mean radius of thrombocytes and/or their aggregates in the blood sample, that an initial volumetric concentration of thrombocytes range from 0.1 to 1%.

These objects are also accomplished by an apparatus for the analysis of thrombocyte aggregation, comprising a means for containing a blood sample and a means coupled thereto for imparting movement to thrombocytes and/or their aggregates in the blood sample, a source of light flux directed at the blood sample and a photo receiver optically coupled thereto for converting the light flux passed through the blood sample into an electric signal corresponding to intensity of the transmitted light flux. According to the invention, the apparatus also comprises a mean intensity forming unit having an input connected to an output of the photo receiver, a circuit for suppressing fluctuations of intensity caused by rotation of non-spherical thrombocytes in the flow having an input connected to the output of the photo receiver, a unit for forming the rms deviation of intensity from the mean intensity having an input connected to an output of the fluctuations suppression circuit, a unit for determining parameters of thrombocyte aggregation corresponding to the mean radius of thrombocytes and/or their aggregates and/or concentration of thrombocytes having inputs connected to outputs of the mean intensity forming unit and rms intensity deviation forming unit.

The mean intensity forming unit preferably comprises a low-pass filter, and the circuit for suppressing intensity fluctuations caused by rotation of non-spherical thrombocytes in the flow preferably comprises a low-cut filter which comprises a filter with a cut-off frequency from 100 to 200 Hz.

The circuit for suppressing intensity fluctuations may comprise a means for detecting a-c component of the electric signal.

The means for detecting a-c component of the electric signal may be in the form of a low-cut filter.

The unit for determining parameters of thrombocyte aggregation corresponding to the mean radius of thrombocytes and/or their aggregates preferably comprises a signal divider having its inputs connected to outputs of the mean intensity forming unit and forming the rms deviation of intensity from the mean intensity, and a squarer having an input connected to an output of the signal divider, an output of the squarer generating a signal proportional to the mean radius of thrombocytes and/or their aggregates.

It is also preferred that the unit for determining parameters of thrombocyte aggregation corresponding to concentration of thrombocytes comprise a memory unit connected to the output of the mean intensity forming unit, a first logarithm computing circuit having an input connected to an output of the memory unit, a second logarithm computing circuit having an input connected to the output of the mean intensity forming unit, a signal subtracter having inputs connected to outputs of the first and second logarithm computing circuits, a second signal divider having a first input connected to an output of the first signal divider, a second input connected to an output of the signal subtracter and an output connected to an input of a second squarer, having an output generating a signal proportional to concentration of thrombocytes.

BRIEF DESCRIPTION OF DRAWINGS

Other objects and advantages of the invention will be apparent from the following specific embodiments illustrated in the accompanying drawings, in which:

FIG. 3 shows curves illustrating variations of the relative dispersion of fluctuations of light flux;

FIG. 4 shows individual units of the apparatus according to the invention;

BEST MODE FOR CARRYING OUT THE INVENTION

A method for the analysis of thrombocyte aggregation comprises taking a blood sample containing thrombocytes and/or their aggregates and placing in into a cell. Light flux is caused to pass through the blood sample placed in the cell to form an optical channel in the blood sample. A flow of thrombocytes and/or their aggregates is created in the blood sample through the optical channel, and the mean intensity of the transmitted light flux I and the rms deviation $\sigma$ of intensity of the transmitted light flux from the mean intensity are concurrently measured. The rms deviation is caused by fluctuations of the number of thrombocytes in the optical channel. Using I and $\sigma$, either the mean radius of thrombocytes and/or their aggregates, or concentration of thrombocytes, or both the mean radius of thrombocytes and/or their aggregates and concentration of thrombocytes are determined. For determining the mean radius of thrombocytes and/or their aggregates, it is expedient to make use of the value of the relative dispersion D of fluctuations of the light flux passed through the blood sample which is determined as the square of the ratio of the rms deviation of intensity of light flux to the mean intensity of the light flux, i.e. $D=[\sigma/\tau]^2$. For determining concentration of thrombocytes, the use is made of the square of the difference between logarithms of the mean intensity I of the light flux passed through the blood sample and intensity $I_o$ of the light flux when there are no thrombocytes in the sample to the relative dispersion D of fluctuations of the light flux.

For a more accurate determination of the mean radius of thrombocytes and/or their aggregates, a volumetric concentration of thrombocytesin a sample of suspension of thrombocytes prepared for the analysis is determines by centrifuging or by a method that gives information on volumetric distribution of platelets. An initial volumetric concentration of thrombocytes is brought to a level within the range from 0.1 to 1% by dilution with a non-thrombocyte plasma. It should be noted that in all cases where the results of determination of the mean raduis of forming aggregates in different samples should be comparable, one must use one and the same value of volumetric concentration of thrombocytes in a blood sample, e.g. 0.25%. The choice of the limit values of the range 0.1 and 1% is due to the fact that with volumetric concentration of thrombocytes under 0.1% thrombocyte concentration does not exceed 50,000 $\mu$l so that the desired accuracy of the optical methods of investigation cannot be ensured. The volumetric concentration of thrombocytes in the blood of a healthy human being is very rarely above 1%.

Figure 1A:
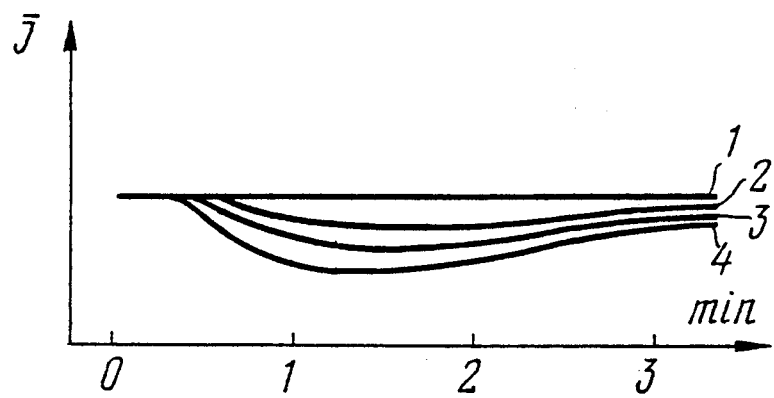
FIG. 1a, b shows time-depending relationships illustrating results of the analysis the thrombocyte aggregation.
Figure 1B:
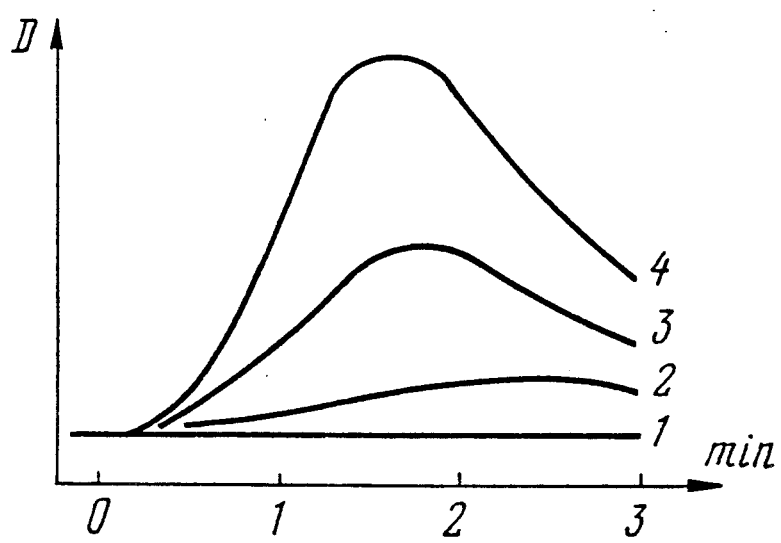

FIG. 1 shows the results of the analysis of thrombocyte aggregation after the action of ADP in different concentrations upon thrombocytes of a healthy human being. Adding ADP to a blood sample in low concentrations (0.1 $\mu$m, 0.15 $\mu$m and 0.2 $\mu$m corresponding to curves 2-4, respectively, wherein curve 1 shows the absence of ADP (0.0 $\mu$m)) intensity I of the light flux passed through the blood sample (FIG. 1a) which cannot be interpreted as a result of formation of aggregates so that one cannot unambiguously judge on the size of thrombocyte aggregates. After the action of such concentrations of ADP, there is a dose-dependent increase in the relative dispersion of fluctuations of intensity of the transmitted light as shown in FIG. 1b (curves 1,2,3 and 4). This is due to an increase in the mean size of thrombocyte aggregates.

It is also apparent from curves 1 through 4 that the mean size of the aggregates reached a maximum value 1-3 minutes after the addition of ADP and then decreases. The control using the scanning electron microscopy showed that after the action of ADP in concentrations from 0.1 to 0.2 $\mu$m aggregates formed in the blood sample which can be recorded by an increase in D so that this parameter (D) can be used for the analysis of thrombocyte aggregation.

Table 1 gives the results of the determination of concentration of thrombocytes, erythrocytes and latex particles of 4 $\mu$m size in carrying out the method and apparatus for the analysis of thrombocyte aggregation according to the invention.

TABLE I

| | Thrombocytes | Erythrocytes | Latex particles |
|---|---|---|---|
| Prior art | $2 \times 10^5 \mu m^{-1}$ | $1.2 \times 10^4 \mu m^{-1}$ | $8 \times 10^3 \mu m^{-1}$ |
| $\frac{(\ln po - \ln p)^2}{V \cdot D}$ | $1.9 \times 10^5 \mu m^{-1}$ | $1.23 \times 10^4 \mu m^{-1}$ | $7.8 \times 10^3 \mu m^{-1}$ |

V is the volume of the optical channel which was equal to 5 m².

Table 2 gives the values of extinction of the same samples of thrombocytes, erythrocytes and latex particles of 4 $\mu$m size as those used for Table 1. The extinction is the logarithm of the ratio of the incident light flux to the transmitted light flux.

TABLE 2

| Thrombocytes | Erythrocytes | Latex particle |
|---|---|---|
| $2.4 \text{ cm}^{-1}$ | $2.2 \text{ cm}^{-1}$ | $2.9 \text{ cm}^{-1}$ |

It will be apparent from Tables 1 and 2 that the measurement results obtained by the prior art method and the method according to the invention are substantially the same, i.e. a change in optical properties of particles does not affect accuracy of readings obtained in using the method and apparatus according to the invention.

Figure 2:
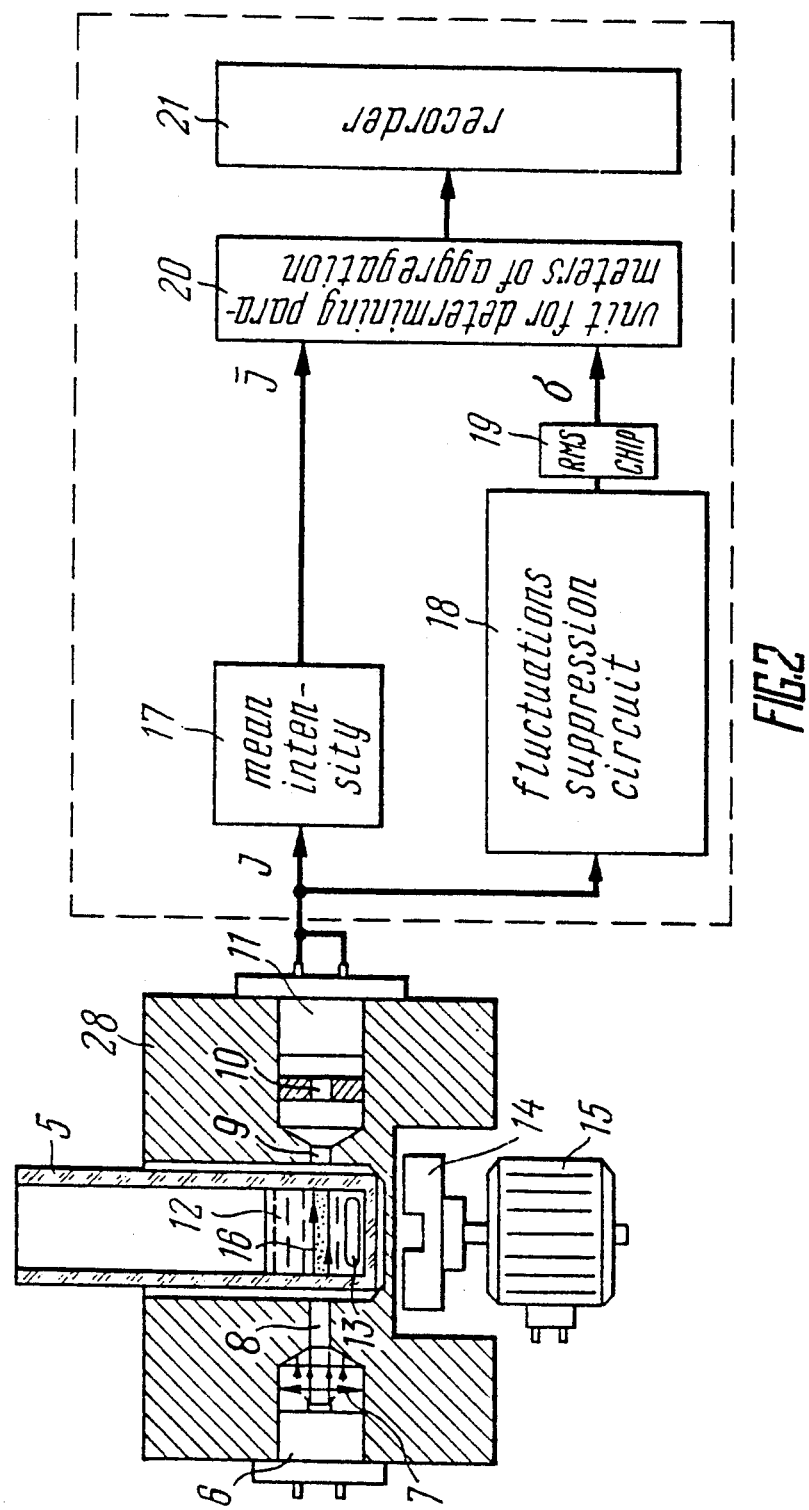
FIG. 2 is a block-diagram of an apparatus for the analysis of thrombocyte aggregation according to the invention.

FIG. 2 shows a block-diagram of an apparatus for the analysis of thrombocyte aggregation. An apparatus comprises a means for containing a blood sample which is in the form of a transparent change cell 5 having a flat bottom wall. A light source is in the form of a semiconductor laser 6. The luminuous element of the laser 6 is positioned in the focus of a short-focus collimation lens 7. The light of the laser 6 collected into a parallel beam passes through an inlet diaphragm 8 and outlet diaphragms 9 and 10. The collimated light from the light source passes through the inlet diaphragm 8, the cell 5 and the outlet diaphragms 9 and 10 to be incident upon a photo receiver 11. The photo receiver converts the light flux incident thereupon into an electric signal.

A blood sample 12 placed in the cell 5 is stirred by means of a mechanism for imparting motion to thrombocytes and/or their aggregates which comprises a magnetic stirrer 13. The magnetic stirrer is driven by a magnet 14 rotated by an electric motor 15.

An optical channel 16 is formed in the blood sample 12 out of the light flux from the laser 6, and a flow of blood particles is formed by the stirrer 13 through this channel.

An output of the photo receiver 11 is connected to an input of a mean intensity forming unit 17 and an input of an intensity fluctuations suppression circuit 18. An output of the circuit 18 is connected to an input of a unit 19 for forming the rms deviation of intensity from the mean intensity.

The apparatus comprises a unit 20 for determining parameters of thrombocyte aggregation having its inputs to which are connected outputs of the units 17 and 18 and an output to which is connected a recorder 21 which be of any appropriate known type, e.g. in the form of a display.

The unit 17 comprises a low-pass filter, the circuit 18 is in the form of a low-cut filter with the cut-off frequency of 100 to 200 Hz.

With a cut-off frequency below 100 Hz fluctuations of intensity cannot be effectively suppressed so that accuracy of measurement is impaired. With a cut-off frequency above 200 Hz the magnitude of useful signal decreases.

FIG. 3 shows time-dependent variations of the relative dispersion of fluctuations of the light flux passed through the blood sample with the use of a low-cut filter having different cut-off frequencies: 50 Hz; 100 Hz; 150 Hz; 200 Hz; and 400 Hz. The influence of platelet shape on the value of $[\sigma/\tau]^2 = D$ was investigated after the action of 0.5 μm of ADP upon thrombocytes. As a result of binding of calcium ions in this medium no aggregation of thrombocytes occurs. In the apparatus according to the invention without a filter (curve 22) and with the use of a filter with the cut-off frequency of 50 Hz (curve 23) a change in configuration of cells influenced the measurement results. When filters with the cut-off frequencies 100 Hz; 150 Hz; 200 Hz; and 400 Hz (curves 24, 25, 26 and 27) were used, changes in configuration of thrombocytes did not influence the results, but with the cut-off frequency of 400 Hz (curve 27) a decrease in the useful signal from the apparatus occured.

The cell 5 (FIG. 2), laser 6, lens 7, diaphragms 8 through 10, and the photo receiver 11 are installed on a base 28, and the diaphragms 8 and 9 are in the form of coaxial apertures made in the base 28.

FIG. 4 shows embodiments of the units 17 and 19 and circuit 18.

The unit 17 comprises an operation amplifier 29 having at the input there of resistors 30 and 31 and capacitors 32 and 33.

The circuit 18 comprises an operation amplifier 34, resistors 35 and 36 and capacitors 37 and 38.

The unit 19 comprises operation amplifiers 39, 40 and 41, resistors 42, 43, 44, 45 and 46, a capacitor 47, and diodes 48, 49, 50, 51 and 52 connected to one another as shown in FIG. 4.

Figure 5:
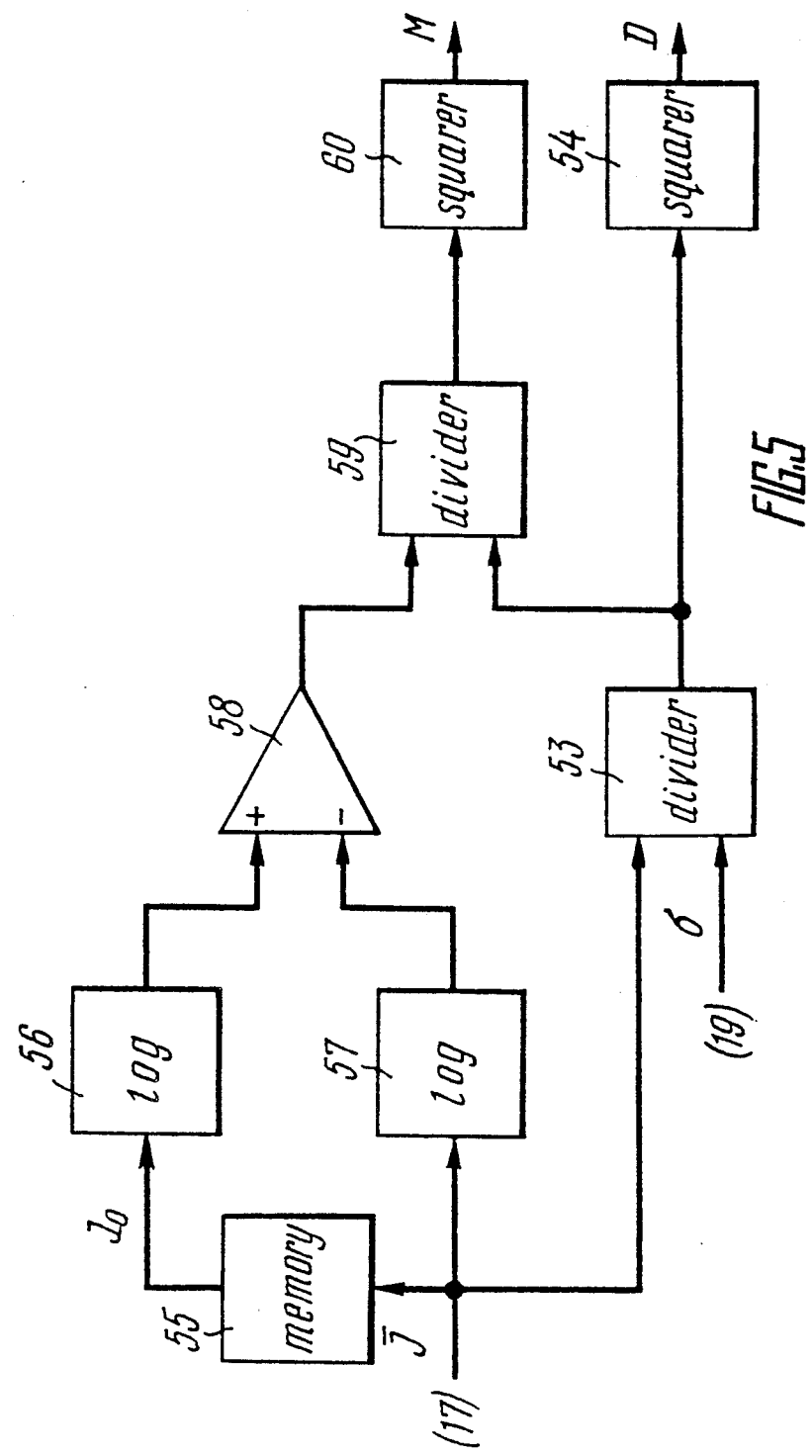
FIG. 5 shows a unit for determining parameters of thrombocyte aggregation according to the invention.

The unit 20 (FIG. 2) for determining parameters of thrombocyte aggregation comprises a divider 53 (FIG. 5) having its inputs connected to outputs of the units 17 and 19 (FIG. 2). A signal corresponding to the formula $\sigma/\tau$ is formed at the output of the divider 53 (FIG. 5) and goes to an input of a squarer 54, and a signal corresponding to the dispersion D of fluctuations of the light flux passed through the blood sample is formed at the output thereof, which is proportional to the mean radius of thrombocytes and/or their aggregates.

For determining concentration of thrombocytes, the unit 20 (FIG. 2) comprises a memory unit 55 (FIG. 5) having its input connected to an output of the unit 17 (FIG. 2), the memory unit storing the value of the mean intensity $1_o$ of the light flux passed through a blood sample that does not contain thrombocytes. The output of the unit 55 is connected to a logarithm computing circuit 56 which, together with a logarithm computing circuit 57 for computing logarithm of the mean intensity 1 of the light flux passed through the blood sample being tested, is connected to inputs of a subtractor 58. An output of the subtractor 58 and the output of the divider 53 are connected to inputs of a divider 59 having an output connected to an input of a squarer 60. A signal M formed at the output of the squarer 60 is proportional to concentration of thrombocytes in the blood sample. As shown in FIG. 2, the circuit 18 comprises a means for detecting a-c component of the electric signal which is in the form of a low-cut filter. As shown in FIG. 4, two low-cut filters are integrated into a single circuit.

The apparatus according to the invention is built around integrated chips and a computer.

The apparatus for the analysis of thrombocyte aggregation functions in the following manner.

The blood sample which is prepared in such a manner as not containing thrombocytes is placed in the cell 5. Light from the source 6 is collected by the short-focus collimation lens 7 into a parallel beam, and the inlet diaphragm 8 forms a light flux in the form of a narrow beam that passes through the blood sample 12 in the cell 5. The light flux then passes through the outlet diaphragms 9 and 10 and is incident upon the photo receiver 11. The light flux forms in the blood sample 12 the optical channel 16. The signal from the output of the photo receiver 11 is fed to the input of the mean intensity forming unit 17 and then goes to the input of the memory unit 55 wherein it is memorized and stored in the form of the signal corresponding to the intensity of the light flux passed through the blood sample 12 that does not contain thrombocytes.

The blood sample that does not contain thrombocytes is then removed from the cell 5, and the blood sample containing thrombocytes for the analysis is placed in the cell 5. The magnetic stirrer 13 is put into the cell, and the electric motor 15 is energized. Light from the source 6 is collected by the short-focus, collimation lens 7 into a parallel beam, and the inlet diaphragm 8 forms a light flux in the form of a narrow beam which passes through the blood sample 12 in the cell 5. The light flux then passes through the outlet diaphragms 9 and 10 and is incident upon the photo receiver 11. The optical channel 16 is formed in the blood sample 12. The signal from the output of the photo receiver 11 is fed to the inputs of the mean intensity forming unit 17 and of the circuit 18 for suppressing fluctuations of intensity. The output signal of the circuit 18 for suppressing fluctuations of intensity is fed to the rms deviation forming unit 19. Movement of thrombocytes and/or their aggregates through the optical channel 16 causes fluctuations of the number of platelets in the optical channel 16. This, in turn, results in the signal $\sigma$ being formed at the output of the rms deviation forming unit 19. The output signals of the rms deviation forming unit 19 and of the mean intensity forming unit 17 are then fed to the inputs of the divider 53. The signal corresponding to the result of the division $\sigma/\tau$ is fed to the input of the squarer 54 and goes, in the form of the signal D proportional to the mean radius of thrombocytes and/or their aggregates, to the recorder 21. The output signal of the mean intensity forming unit 17 is also fed to the input of the logarithm computing circuit 57 and further to one of the inputs of the subtractor 58. The stored signal from the output of the memory unit 55 is fed to the logarithm computing circuit 56 and further to the input of the subtractor 58. The output signal of the subtractor 58 is fed to one of the inputs of the divider 59. The output signal from the first divider 53 is fed to the second input of the divider 59. The output signal from the divider 59 is fed to the squarer 60 and is then fed, in the form of a signal $$M = \frac{(\ln \tau_0 - \ln \tau)^2}{D}$$

proportional to concentration of thrombocytes, to the recorder 21.

The values of the above described signals D and M are used for the quantitative evaluation of thrombocyte aggregation during spontaneous aggregation or after the administration of aggregation inducers. The data obtained by using the method and apparatus according to the invention make it possible to determine the condition of hyper-or hypoactivity of thrombocytes. This is important in diagnosing hematologic diseses (Glanzmahh's thrombasthenia, Bernard-Soulier syndrome and the like), cardiovascular diseases (ischemic heart disease, cardiomyopathy, hypertension, and the like) and a number of other diseases.

The use of the invention makes it possible to diminish the risk factor of thromboembolic complications and to find ways of medicamentous correction of disruptions of thrombocyte activity in patients. Widespread use of the invention is expected for screening new medicines and for controlling condition of thrombocyte mass prepared for blood transfusion.

The invention makes it possible to carry out a continuous monitoring of the mean radius of thrombocytes and/or their aggregates in a blood sample being tested. This facility makes it possible to characterize in a more complete and accurate manner changes in the functional activity of thrombocytes, high sensitivity of the method and apparatus for the analysis of aggregation, hence the ability of determining the degree of aggregation of thrombocytes after the action of inducers in low concentrations makes it possible to diagnose the condition of hyperactivity of thrombocytes in case of hypertension, at initial stages of dilatative cardiomyopathy and a number of other cardiovascular diseases.

In addition, the invention makes it possible to determine concentration of thrombocytes in a blood sample being tested with a high accuracy (up to 0.1-1%) without any preliminary measurements nor any additional information on the blood sample. Independence of readings of the optical properties of platelets allows the method and apparatus to be used for the determination of concentration and analysis of aggregation of any other blood cells (erythrocytes, leukocytes) and similar biological tissues. Simplicity, high speed and high informative value allow the invention to be widely used in the clinical and laboratory practice.

INDUSTRIAL APPLICABILITY

This invention can be used for diagnosis of cardiovascular conditions.

We claim:

1. A method of analyzing blood platelet aggregations, comprising the steps of passing a light flux through a blood sample (12) containing blood platelets and/or aggregates thereof and measuring the intensity of the flux which has passed through the blood sample (12), wherein an optical channel (16) is formed having the required geometry, passing the blood platelets and/or aggregates thereof through the optical channel passing through the blood sample (12), measuring the mean intensity of the light flux passed through the blood sample (12) and the RMS deviation of intensity of the transmitted light flux caused by fluctuations in the number of blood platelets and/or aggregates thereof in the optical channel (16), and determining the mean radius of blood platelets and/or aggregates thereof and/or the concentration of blood platelets in the blood sample (12) on the basis of the measured mean intensity and the measured RMS deviation of intensity of the transmitted light flux.

2. A method as claimed in claim 1, wherein the step of determining the mean radius of blood platelets and/or aggregates thereof further comprises using the relative dispersion of fluctuations of the light flux passed through the blood sample (12), which is equal to the square of the ratio between the measured RMS deviation of intensity and the mean intensity.

3. A method as in claim 1 wherein in order to determine the blood platelet concentration, a blood sample that contains no blood platelets is placed into the optical channel and light flux intensity is measured, then the blood sample containing no blood platelets is replaced by the blood sample containing blood platelets for the analysis, and use is made of the ratio of the square of the difference between the logarithms of the mean intensity of the light flux passed through the blood sample (12) and the intensity of the light flux in the blood sample (12) containing no blood platelets to a relative dispersion of fluctuations of the light flux which is equal to the square of the ratio between the measured RMS deviation of intensity and the mean intensity.

4. A method as in claim 2 wherein in order to determine the blood platelet concentration, a blood sample that contains no blood platelets is placed into the optical channel and the light flux intensity is measured, then the blood sample containing no blood platelets is replaced by the blood sample containing blood platelets for the analysis, and use is made of the ratio of the square of the difference between the logarithms of the mean intensity of the light flux passed through the blood sample (12) and the intensity of the light flux in the blood sample (12) containing no blood platelets to the relative dispersion of fluctuations of the light flux which is equal to the square of the ratio between the measured RMS deviation of intensity and mean intensity.

5. A method as claimed in claims 1 or 2, wherein, in order to specify the mean radius of blood platelets and/or their aggregates in the blood sample (12), the initial volumetric concentration of blood platelets is taken within the range of from 0.1 to 1%.

6. An apparatus for analysis of a blood platelet aggregation, comprising a means (5) containing a blood sample (12) and a mechanism to impart motion to blood platelets and/or their aggregations in said blood sample (12), a source (6) of the light flux directed to the blood sample (12), a photoreceiver (11) optically connected with the source (6) and intended to transform the light flux passed through the blood sample (12) into an electric signal corresponding to the intensity of the transmitted light flux, wherein it also comprises a mean intensity forming unit (17) having its input connected to the output of the photoreceiver (11), a circuit (18) to suppress intensity fluctuations caused by the rotation of non-spherical blood platelets in the flux, having its input connected to the output of the photoreceiver (11), a unit (19) to form the RMS deviation of the intensity from the mean intensity and having its input connected to an output of the intensity fluctuation suppression unit (18); a unit (20) to determine those parameters of a blood platelet aggregation, which are indicative of the mean radius of blood platelets and/or their aggregates and/or the concentration of blood platelets, which has its inputs connected to outputs of the mean intensity forming unit (17) and the intensity RMS deviation forming unit (19).

7. An apparatus as claimed in claim 6, wherein the mean intensity forming unit (17) comprises a low-pass filter.

8. An apparatus as claimed in claim 6 or 7, wherein the circuit (18) for suppression of intensity fluctuations caused by rotation of spherical blood platelets comprises a low-cut filter.

9. An apparatus as claimed in claim 8, wherein the low-cut filter has a cut-off frequency of from 100 to 200 Hz.

10. An apparatus as claimed in claim 6 or 7, wherein the intensity fluctuation suppression circuit (18) comprises a means for detecting the variable component of the electrical signal.

11. An apparatus as claimed in claim 10, the means for detecting the variable component of the electrical signal is a low-cut filter.

12. An apparatus as claimed in 6 or 7, wherein the unit (20) for determination of blood platelet aggregation parameters indicative of the mean radius of blood platelets and/or their aggregates comprises a signal divider (53) having its inputs connected to outputs of the mean intensity forming unit (17) and the unit (19) forming the RMS deviation of intensity from the mean intensity, and a squarer (54) having its input connected to the output of the divider (53) and whose output is a signal proportional to the mean radius of blood platelets and/or their aggregates.

13. An apparatus as claimed in claim 12, wherein the blood platelet aggregation parameter determination unit (20) comprises a memory unit (55) connected to the output of the mean intensity forming unit (17), a first logarithm computing unit (56) whose input is connected to the output of the memory unit (55), a second logarithm computing unit (57) whose input is connected to the output of the mean intensity forming unit (17), a subtracting circuit (58) whose inputs are connected to output of the first and second logarithm computing circuits (56, 57), a second divider (59) having one input connected to the output of the first divider (53), its second input connected to the output of the subtracting circuit (58), and its output connected to the input of the second squarer (60) whose output is a signal proportional to the concentration of blood platelets.

* * * * *